United States Patent [19]

Thompson

[11] Patent Number: 5,699,787
[45] Date of Patent: Dec. 23, 1997

[54] MOUTHPIECE FOR ENDOTRACHEAL TUBE

[76] Inventor: Clarence Thompson, Cumberland Anesthesia, P.O. Box 4338, Oneida, Tenn. 37841

[21] Appl. No.: 665,507

[22] Filed: Jun. 20, 1996

[51] Int. Cl.⁶ .......................... A61M 25/01; A61M 31/00
[52] U.S. Cl. .................. 128/200.26; 128/207.14; 604/79; 604/174
[58] Field of Search .................. 128/207.14, 207.17, 128/DIG. 911, DIG. 912, 200.24, 200.26; 604/77, 79, 283, 174, 179, 180

[56] References Cited

U.S. PATENT DOCUMENTS

| | | | |
|---|---|---|---|
| 3,760,811 | 9/1973 | Andrew | 128/207.17 |
| 4,327,721 | 5/1982 | Goldin et al. | 128/207.15 |
| 4,360,025 | 11/1982 | Edwards | 604/180 |
| 4,774,944 | 10/1988 | Mischinski | 128/207.17 |
| 4,896,667 | 1/1990 | Magnuson et al. | 128/207.17 |
| 5,042,477 | 8/1991 | Lewis . | |
| 5,069,206 | 12/1991 | Crosbie | 128/207.17 |
| 5,076,269 | 12/1991 | Austin | 128/207.17 |
| 5,123,410 | 6/1992 | Greene et al. | 128/207.17 |
| 5,143,062 | 9/1992 | Peckham | 128/207.14 |
| 5,146,916 | 9/1992 | Catalani . | |
| 5,174,284 | 12/1992 | Jackson . | |
| 5,181,508 | 1/1993 | Poole, Jr. . | |
| 5,207,655 | 5/1993 | Sheridan | 604/247 |
| 5,237,988 | 8/1993 | McNeese . | |
| 5,305,742 | 4/1994 | Styers et al. | 128/207.17 |
| 5,309,905 | 5/1994 | Teves . | |
| 5,311,864 | 5/1994 | Huerta . | |
| 5,320,097 | 6/1994 | Clemens et al. | 128/207.17 |
| 5,402,776 | 4/1995 | Islava . | |
| 5,490,504 | 2/1996 | Vrona et al. | 128/207.17 |
| 5,551,421 | 9/1996 | Noureldin et al. | 128/207.17 |
| 5,555,881 | 9/1996 | Rogers et al. | 128/207.17 |

FOREIGN PATENT DOCUMENTS

| | | |
|---|---|---|
| 200470 | 5/1986 | European Pat. Off. . |
| 2164565 | 3/1986 | United Kingdom . |

*Primary Examiner*—Vincent Millin
*Assistant Examiner*—Robert N. Wieland
*Attorney, Agent, or Firm*—Richard C. Litman

[57] ABSTRACT

An endotracheal system is disclosed which contains a contoured mouthpiece capable of fitting between a patient's teeth. The endotracheal system also provides a medication injection line capable of delivering precise doses of medication directly to the patients lungs. The medication may also be delivered in spray form when necessary. The endotracheal system includes a number of arresting elements, attached to the mouthpiece, which are capable of restricting the motion of the endotracheal tube. The endotracheal system may be secured to the patient by means of a flexible cord such as umbilical tape.

15 Claims, 6 Drawing Sheets

MOUTHPIECE FOR ENDOTRACHEAL TUBE

BACKGROUND OF THE INVENTION

1. Field of the Invention

The present invention relates to endotracheal tubes and their associated support structures. The invention relates specifically to an endotracheal system having a contoured mouthpiece to be fitted between a patient's teeth and allowing the passage of an endotracheal tube. The invention also provides a medication injection line that allows precise dosages of medication to be delivered directly to the lungs.

2. Description of the Prior Art

Conventional systems for tracheal intubation are employed routinely by health care professionals in hospital settings. The function of tracheal intubation is to provide mechanical assistance to patients for their secure airway and respiration functions. If mechanical assistance is not provided, the patient will exhibit respiratory distress. The situation could progress to respiratory arrest and even death. Consequently, mechanical assistance is imperative to keeping the airways open.

Such mechanical assistance is effected by an endotracheal tube originating from outside of the patient and extending into the patient's trachea. The endotracheal tube is inserted in the mouth and passed through the larynx into the trachea. The endotracheal tube is typically provided with an inflatable cuff when a sealed airway is required for mechanical ventilation. Once inflated, the cuff fills the space between the outside of the tube and the trachea. The exterior end of the tube is then coupled to a ventilation source for the administration of oxygen, air, or other gases.

It is a conventional practice to secure medical tubes which are to be disposed externally of a patient with an adhesive tape which is wrapped around the tubing and extended therefrom so that it may be adhered to the skin of the patient. However, such an approach is often uncomfortable to the patient. Furthermore, removal of the adhesive tape often causes irritation and infection, in severe cases, to the area where the tape was secured.

Frequently, the tape becomes loose from movement of the patient's head and allows the tube to migrate upward, sideways, or drift downward, thereby appreciably reducing the effectiveness of the tube for providing the needed airflow. More importantly, the tube may descend into one of the bronchi and cause one of the patient's lungs to collapse. It is therefore essential that the medical attendant be continually vigilant in inspecting the adhesive tape and insuring that the endotracheal tube remains immovably secured. This task can often prove difficult to the medical attendant who must oversee a great number of patients.

Often when a patient has suffered a heart attack, it is necessary to perform an intubation procedure while the patient is unconscious. As the patient starts to regain consciousness, the endotracheal tube can sometimes cause undue stimulation of the parasympathetic nervous system, which may slow the heart rate. In addition, the patient's gag reflex is increased which places stress on the heart. The use of a bite block can often reduce this phenomenon.

In many situations where an endotracheal tube is used, it is also necessary to introduce medication to the patient. In hospital settings, where environmental conditions are excellent, intravenous injections are performed routinely for the most rapid administration of life-saving drugs even when a patient is being assisted by an endotracheal tube. In pre-hospital settings, endotracheal tubes are also employed by paramedics or the like. Similar to the hospital setting, the preferred method of administering drugs is intravenously, although alternative methods are being sampled. One such method is intratracheal drug administration. Intratracheal drug administration allows the drug to enter the blood stream immediately due to the direct relation between the lungs and the heart.

While the prior art discloses numerous types of endotracheal tubes and associated support structures, most are suited only for the evacuation of fluids and local anesthesia. For example, U.S. Pat. No. 5,042,477 issued on Aug. 27, 1991, to Lewis discloses a medical tube holder for securing endotracheal tubes and the like.

The tube holder has an elongated tube made of elastomeric, flexible material with a hollow interior and a slit formed transversely to a longitudinal axis of the tubing at the middle portion of the tubing. A securing strap is threaded through the tubing with the middle portion of the strap extending through the slit to form a loop through which the medical tube is inserted. The flexible material is brought around the patient's body and tied together in order to secure the tube relative to the patient's body.

U.S. Pat. No. 5,146,916 issued on Sep. 15, 1992, to Catalani discloses an endotracheal tube equipped for delivering a drug externally of the tube. The endotracheal tube includes a tube body having proximal and distal ends, and at least one flexible irrigation cannula extending along the endotracheal tube's body to its distal end. An irrigation diffuser is attached to the irrigation cannula for spraying a drug externally. The endotracheal tube is particularly useful for the repeated administration of local anesthetics.

U.S. Pat. No. 5,174,284 issued on Dec. 29, 1992, to Jackson discloses a bite block to prevent a patient from biting into an instrument inserted through the mouth during a medical procedure. The bite block includes a sloping channel against which the patient is to bite. As the patient bites on the block, it becomes more firmly seated in the mouth and the patient's tongue is further depressed.

U.S. Pat. No. 5,181,508 issued on Jan. 26, 1993, to Poole, Jr. discloses a drug administering endotracheal respiration system. The system is useful in administering drugs into the lungs of a patient while maintaining the flow of life supporting gases into the lungs via a ventilation apparatus.

U.S. Pat. No. 5,237,988 issued on Aug. 24, 1993, to McNeese discloses a device for immovably securing an endotracheal tube after it has been inserted into the patient's airway. A pair of supports are removably fastened to the inlet of the tube, while a belt is secured to the supports and snugly positioned around the neck of the patient. An adhesive strip is positioned on the belt for adhering to the back of the patient's neck.

U.S. Pat. No. 5,309,905 issued on May 10, 1994 to Teves discloses a connector for endotracheal tubes. The connector is particularly useful for use with tubes which include an integral auxiliary lumen. The connector is tubular in shape and includes a tubular mounting member extending from its proximal end, and a tubular mounting member extending from its distal end for connecting the endotracheal tube to an auxiliary source. A bore extends from the proximal to the distal end of the connector and includes an auxiliary mounting member at each end for connecting the auxiliary lumen.

U.S. Pat. No. 5,311,864 issued on May 17, 1994, to Huerta discloses an apparatus for safe and effective evacuation of fluids or to dispense medication to a patient undergoing breathing assistance. The apparatus includes an evacuation sheath, a balloon cuff lumen, and an optional lumen with a reinforced balloon cuff upper end which promotes uninterrupted breathing assistance and balloon cuff operations. The invention may also be provided with an auxiliary tracheal plate for sealing a tracheal incision.

U.S. Pat. No. 5,402,776 issued on Apr. 4, 1995, to Islava discloses an endotracheal tube holder including a face plate assembly which is attached to a patient's head by an adjustable headband. The face plate assembly includes a plate adapted to be positioned over the patient's mouth and includes an opening for access to the patient's mouth. A bite block is secured to the inner surface of the face plate in order to keep the patient's mouth open.

United Kingdom Patent #2,164,565 issued on Mar. 26, 1986, to Collins, et al. discloses an endotracheal tube assembly having an inflatable cuff. The cuff is inflated via an inflation line partially disposed within the wall of the endotracheal tube.

European Patent Application #200,470 published on Nov. 5, 1986, to Waller discloses a support for a tracheotomy or endotracheal tube. The support includes a band of flexible material which wraps around the patient's head. The band includes an aperture portion through which an endotracheal tube may be passed. The support may also be provided with a base member which abuts a patient's throat when a tracheotomy is performed.

None of the above inventions and patents, taken either singly or in combination, is seen to describe the instant invention as claimed.

SUMMARY OF THE INVENTION

Accordingly, it is a principal object of the invention to provide a mouthpiece for an endotracheal system.

It is another object of the invention to provide a mouthpiece for an endotracheal system which prevents a patient from biting down on the endotracheal tube.

It is a further object of the invention to provide a mouthpiece for an endotracheal system which secures the endotracheal tube from unintentional movement.

Still another object of the invention is to provide an endotracheal system having means for delivering medication to a patient's lungs.

It is an object of the invention to provide improved elements and arrangements thereof in an apparatus for the purposes described which is inexpensive, dependable and fully effective in accomplishing its intended purposes.

In accordance with the objects of the invention, there is provided a mouthpiece for an endotracheal tube. The mouthpiece includes a bite block which has a proximal surface, a distal surface, and a central aperture. The central aperture is of a predetermined diameter for receiving an endotracheal tube. A number of arresting elements are coupled to the bite block. Each arresting element contains a frictional pad for restricting the motion of the endotracheal tube. Each arresting element is also capable of detachably engaging the bite block. When an arresting element engages the bite block, it is locked in a position where the frictional pad is in contact with the endotracheal tube, thereby restricting motion of the tube. When the arresting element is disengaged from the bite block, the frictional pad is no longer in contact with the endotracheal tube and the tube is somewhat free to move within the central aperture of the bite block.

The bite block is designed to withstand the forces capable of being exerted by a patient's jaw. This in turn prevents a trauma patient from accidentally biting down on the endotracheal tube and depriving himself of life saving gases. The bite block may also be provided with an external layer of resilient material for the patient to comfortably bite into, while still having a rigid inner layer which protects the endotracheal tube.

In accordance with another object of the invention, the mouthpiece is provided with means to secure it to the patient. With the mouthpiece secured, the endotracheal tube is incapable of being accidentally removed from the patient's mouth or inserted further into the trachea. This requires less supervision from attending health care personnel to assure that the endotracheal tube does not exit the patient's trachea and damage the vocal cords or descend into one of the patient's bronchi. In one embodiment of the invention, the mouthpiece is secured to the patient by using umbilical tape. The umbilical tape is secured to a first arresting element, passed behind the patient's head, and secured to a second arresting element.

In accordance with another object of the invention, an endotracheal system is provided. The system includes an endotracheal tube having a proximal end and a distal end. The distal end of the endotracheal tube also includes an exit port. The endotracheal tube has a wall which is defined by the area between its inner and outer diameters. A balloon is attached around the outer surface of the endotracheal tube at the distal end. The balloon is capable of being inflated by an external supply of gas. It is also possible to deliver medication directly into the patient's lungs via the endotracheal tube.

The system also includes a mouthpiece which has a bite block and at least two arresting elements coupled to the bite block. The bite block has a proximal surface, a distal surface, and a central aperture suitable for receiving the endotracheal tube. Each of the arresting elements is provided with a frictional pad for restricting the motion of the endotracheal tube inserted through the bite block. The arresting elements are capable of engaging the bite block and being locked in a position to effectuate the necessary friction on the endotracheal tube.

In order to deliver medication directly to the patient's lungs and to inflate the balloon, two lumens are disposed within the wall of the endotracheal tube. The first lumen is used to deliver medication and extends to the exit port of the endotracheal tube. The second lumen is used to inflate the balloon and extends to the area near the distal end corresponding to the location of the balloon. The lumens enter the wall of the endotracheal tube through a first and second entry point near the proximal end of the endotracheal tube.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
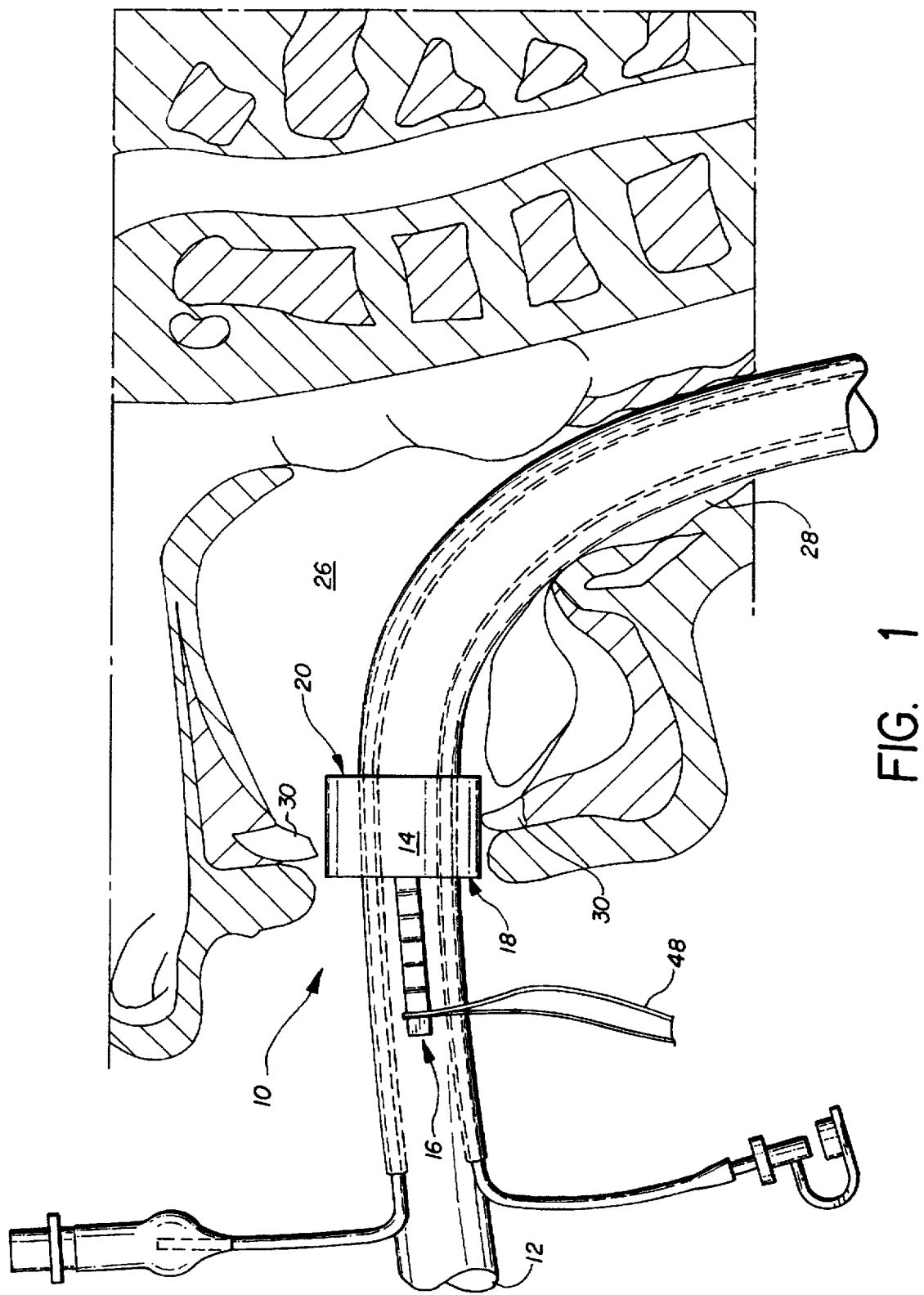
FIG. 1 is a partially fragmented environmental view of an endotracheal system of the present invention.

With reference to the drawings and initially to FIG. 1, there is provided a mouthpiece 10 for an endotracheal tube 12. The mouthpiece 10 includes a bite block 14 and a plurality of arresting elements 16 attached to the bite block 14. The arresting elements 16 are used to restrict motion of the endotracheal tube 12.

The bite block 14 has a proximal surface 18 and a distal surface 20. The bite block 14 also contains a central aperture through which the endotracheal tube 12 is inserted. The bite block 14 is designed to fit between a patient's teeth 30. In order to prevent a patient from moving their jaw and accidentally biting on the endotracheal tube 12, the bite block 14 should be of a length sufficiently greater than the forward distance which an average patient's jaw can travel. It is preferred that the bite block 14 be made of a clear material in order to facilitate reading the measurements inscribed on the endotracheal tube 12.

The bite block 14 may be constructed of any material which is capable of withstanding the forces which might be applied upon it by a patient's jaw. The bite block 14 may also have a variety of cross-sectional areas, such as square or rectangular, so long as the patient is capable of biting on the exterior.

Figure 2:
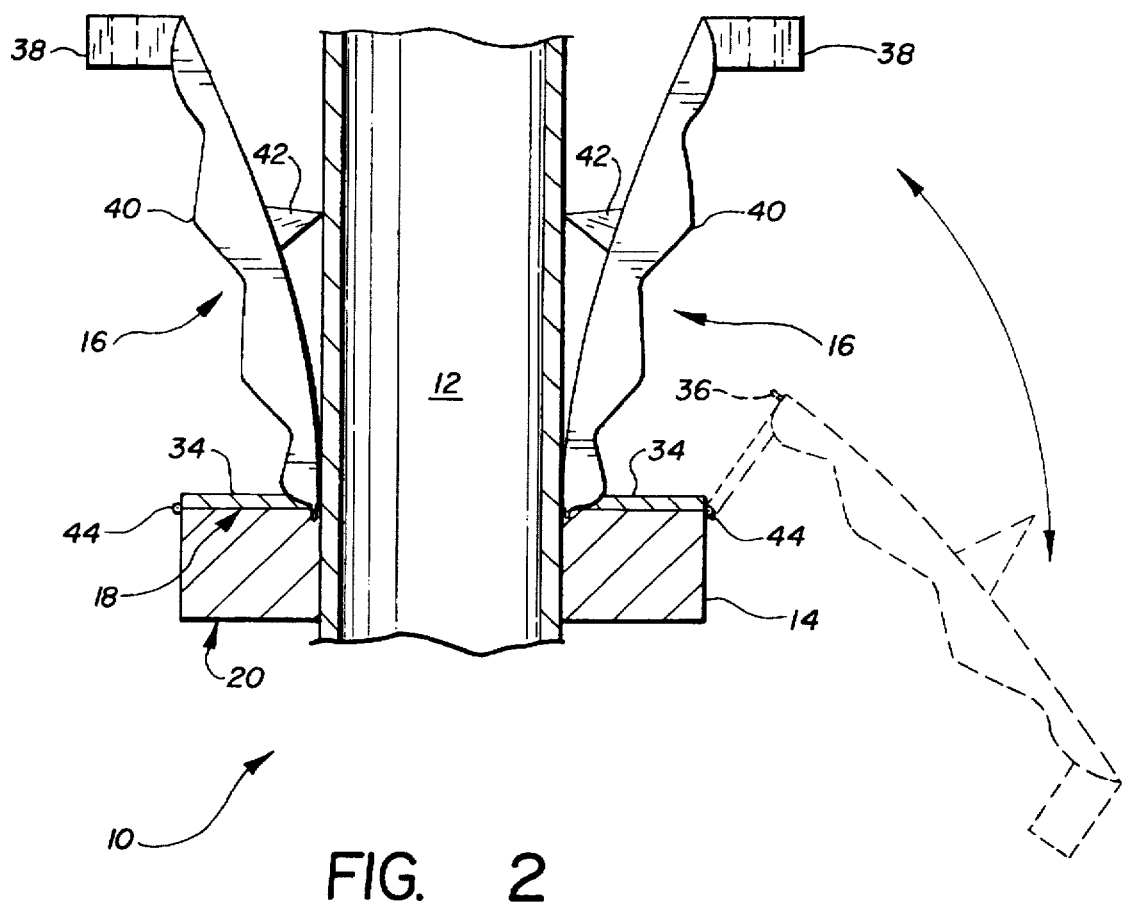
FIG. 2 is a sectional view detailing the mouthpiece of the present invention.

A number of arresting elements 16 are attached to the bite block 14. As seen more particularly with reference to FIG. 2, each arresting element 16 has a base portion 34, an upstanding leg 40, and a shoulder 38. Each arresting element 16 is coupled to the bite block 14. The embodiment of the mouthpiece 10 illustrated FIG. 2 incorporates a hinge 44 as the means for coupling each of the arresting elements 16 to the bite block 14. The hinge 44 provides a pivotal connection between the arresting elements 16 and the bite block 14 as illustrated by the phantom lines.

A fitted extension 36 originates from the base portion 34 of the arresting element 16 and extends in a perpendicular manner. A mating recess is provided on the proximal surface 18 of the bite block 14 for receiving the fitted extension 36. The arresting element 16 may be pivoted until it engages the mating recess. Once engaged, a predetermined force is required to disengage the arresting element 16. Each arresting element 16 includes a resilient friction pad 42 capable of contacting the endotracheal tube 12. When the arresting elements 16 are engaged with the bite block 14, the friction pads 42 are placed in snug contact with the endotracheal tube 12. The combined force placed on the endotracheal tube 12 by all of the friction pads 42 is sufficient for keeping the endotracheal tube 12 in the desired stationary position.

In operation, a health care attendant would first disengage the arresting elements 16 from the bite block 14 and insert the endotracheal tube 12 through the aperture of the bite block 14. The endotracheal tube 12 is then inserted through the patient's oral cavity 26 and into the trachea 28 as illustrated in FIG. 1. As the endotracheal tube 12 is further inserted into the trachea 28, the mouthpiece 10 may be continually adjusted to compensate so that it remains within contact of the patient's teeth 30. Next, the arresting elements 16 are pivoted to engage the bite block 14 so that the friction pads 42 are in contact with the endotracheal tube thus preventing accidental movement thereof. As seen in FIG. 1, umbilical tape 48 or other means, such as a string or cord, may be provided to secure the mouthpiece 10 to the patient's head. Traditionally, adhesive tape is used to secure the endotracheal tube to a patient's face.

Figure 3:
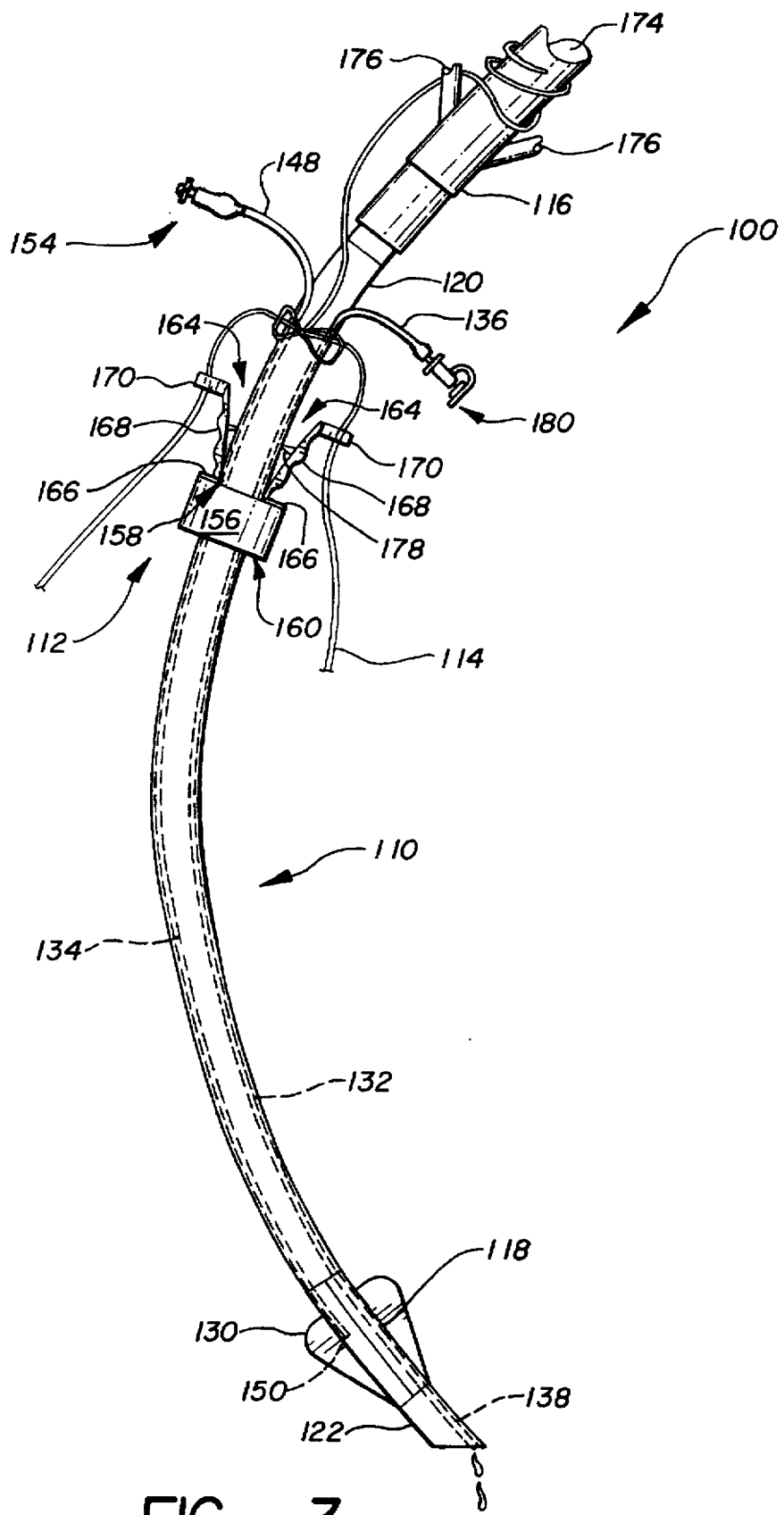
FIG. 3 is a side elevational view of an endotracheal system according to the present invention.

Turning now to FIG. 3, there is provided an endotracheal system 100 which incorporates a mouthpiece 112 and is capable of delivering medication directly into the lungs of a patient. The endotracheal system 100 includes an endotracheal tube 110, a mouthpiece 112, a connector 116 for attaching the endotracheal tube to an external gas supply (not shown), and umbilical tape 114 or other means, such as a string or cord, for securing the endotracheal system 100 to the patient.

The endotracheal tube 110 has a proximal end 118 and a distal end 120. Art exit port 122 is attached to the distal end 120 of the endotracheal tube 110. The endotracheal tube 110 has an inner diameter and an outer diameter. The area between the inner and outer diameters defines a wall. A balloon 130 is attached to the outer surface of the endotracheal tube 110 at the distal end 120.

A first lumen 132 is provided for delivering medication to the patient's lungs. The first lumen 132 has a proximal end 136 and a distal end 138. The first lumen 132 is disposed within the wall of the endotracheal tube 110. The distal end 138 of the first lumen 132 extends to the exit port 122 of the endotracheal tube 110. The proximal end 136 of the first lumen 132 is external of the patient and the endotracheal tube 110. A first entry point is provided in the wall of the endotracheal tube 110 for the first lumen 132 to enter through. A syringe permeable diaphragm assembly 180 is attached to the proximal end 136 of the first lumen 132 so that medication may be directed to the patient.

A second lumen 134 is provided for inflating the balloon 130. The second lumen 134 is also disposed in the wall of the endotracheal tube 110. The second lumen 134 has proximal end 148 and a distal end 150. The proximal end 148 of the second lumen 134 originates external of the patient and the endotracheal tube 110 while the distal end 148 of the second lumen 134 terminates in the balloon 130. A second entry point is provided in the wall of the endotracheal tube 110 through which the second lumen 134 enters. An adapter 154 is attached at the proximal end 148 of the second lumen 134 for attaching a gas supply (not shown) to inflate the balloon 130.

The mouthpiece 112 of the endotracheal system 100 includes a bite block 156 and a plurality of arresting elements 164. The bite block 156 has a proximal surface 158, a distal surface 160, and a central aperture through which the endotracheal tube 110 is inserted. Each of the arresting elements 164 includes a base portion 166, an upstanding leg 168, and a shoulder 170. The shoulder 170 of each arresting element 164 also includes a vertical groove. A friction pad 178 is also attached to the upstanding leg 168 of each arresting element 164 in order to secure the endotracheal tube 110.

A connector 116 is also provided for attaching the endotracheal tube 110 to an external gas supply (not shown). The connector 116 includes a first passageway 174 which functions as the main supply line to the endotracheal tube 110. Auxiliary passageways 176 which are smaller in diameter may also be provided in the connector 116. The auxiliary passageways 176 may serve numerous functions such as monitoring the level of carbon dioxide being exhaled by the patient.

Umbilical tape 114 or other means, such as a string or cord, may be used to secure the endotracheal system 100 to the patient as illustrated in FIG. 3. The umbilical tape 114 would first be passed through the vertical groove in the shoulder 170 of one of the arresting elements 164 and wrapped around the same shoulder 170 several times so that a short portion and an long portion remain free. The long portion of the umbilical tape 114 is then passed behind the head of the patient and wrapped in a similar manner around the shoulder 170 of another arresting element 164. Next, the long portion of the umbilical tape 114 is wrapped several times around the endotracheal tube 110 and releasably tied to the short portion. The long portion of the umbilical tape 114 may then be wrapped several times around the connector 116 in order to secure the entire endotracheal system 100 to the patient.

Figure 4:
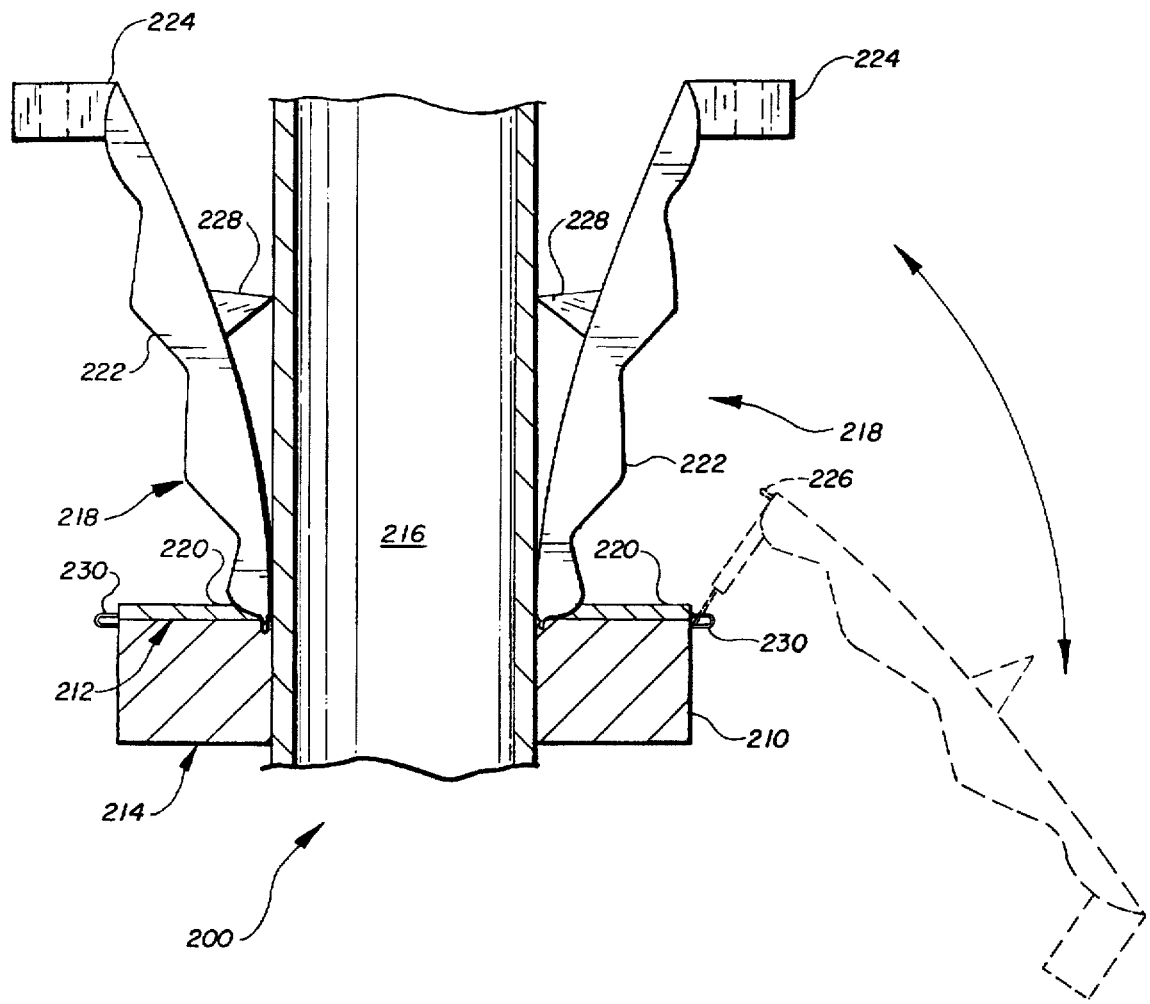
FIG. 4 is a sectional view of an alternative embodiment of the mouthpiece utilizing a flexible material to interconnect the bite block and the arresting element.

Turning now to FIG. 4, there is shown an alternative embodiment of a mouthpiece 200. The mouthpiece 200 contains a bite block 210 which has a proximal surface 212 and a distal surface 214. The bite block 210 contains a central aperture through which an endotracheal tube 216 may be passed. The arresting elements 218 of this particular embodiment are coupled to the bite block 210 by means of a band 230 of flexible material. Each arresting element 218 includes a base portion 220, an upstanding leg 222, and a shoulder 224. A fitted extension 226 extends from the base portion 220 and is capable of engaging a mating recess contained on the proximal surface 212 of the bite block 210. A friction pad 228 is attached to the upstanding leg 222 of each arresting element 218. When the fitted extension 226 of the arresting element 218 engages the mating recess of the bite block 210, the friction pads 228 are pushed snugly against the endotracheal tube 216.

Figure 5:
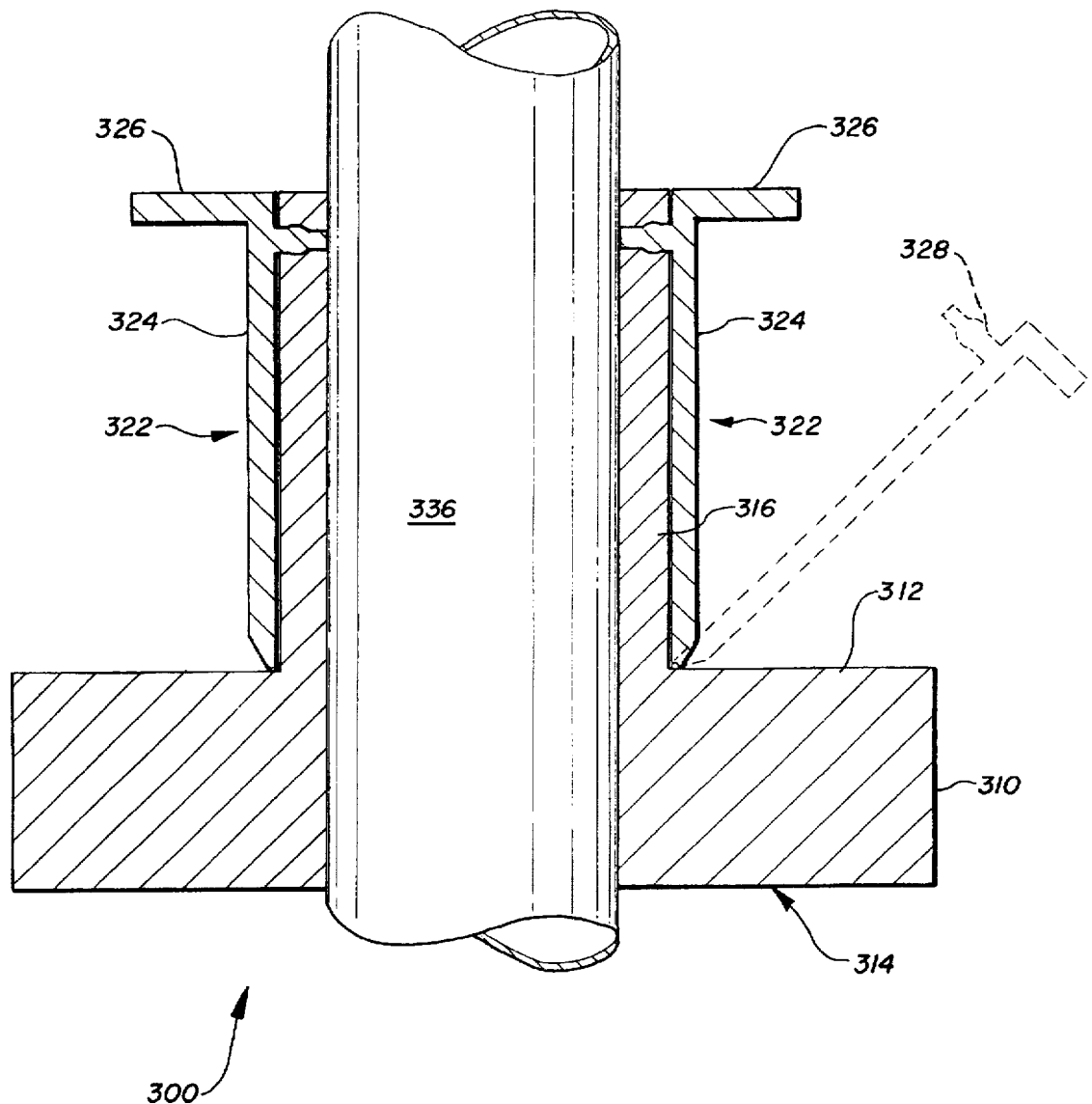
FIG. 5 is a sectional view of an alternative embodiment of the mouthpiece of the present invention.

FIG. 5 illustrates another embodiment of a mouthpiece 300. The mouthpiece 300 is shown to include a bite block 310 which has a proximal surface 312 and a distal surface 314. The bite block 310 also contains a central aperture. A tubular extension 316 originates from the proximal surface 312 of the bite block 310. The tubular extension 316 has an inner diameter identical to the diameter of the central aperture. The outer diameter of the tubular extension 316 is significantly less than that of the bite block 310. An endotracheal tube 336 may be passed through the central aperture of the bite block 310 and the inner diameter of the tubular extension 316. The arresting elements 322 of this particular embodiment are pivotally coupled to the bite block 310 at the point of origination of the tubular extension 316. Each arresting element 322 includes an arm 324 and a shoulder 326. A fitted friction pad 328 is attached to the arm of each arresting elements 322. The tubular extension 316 contains a plurality of mating bores for receiving each of the fitted friction pads 328. When the fitted friction pad 328 of the arresting element 322 engages the mating bore of the bite block 310, the fitted friction pad 328 is pushed snugly against the endotracheal tube 336.

Figure 6:
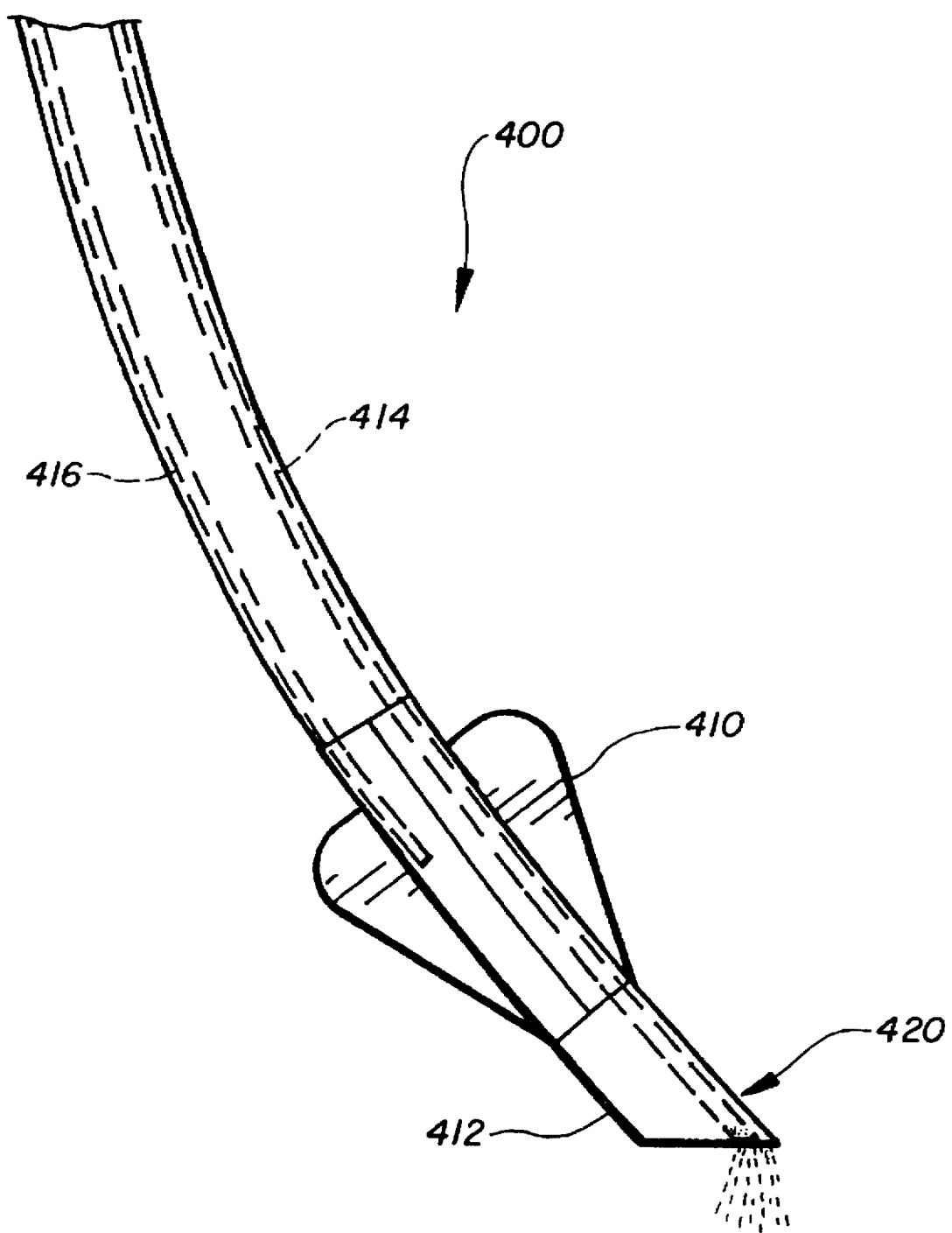
FIG. 6 is a partially fragmented side elevational view of an alternative embodiment of the present invention capable of delivering medication in a spray form.

In certain situations, it may be desirable to deliver medication in a spray, or atomized, form to a patient. FIG. 6 illustrates an embodiment of the endotracheal system which facilitates this procedure. FIG. 6 shows the distal portion of an endotracheal tube 400. A balloon 410 is attached to the periphery of the distal portion 400. An exit port 412 is integrally attached to the distal end 400 of the endotracheal tube and extends therefrom. A first and second lumen 414, 416 are disposed within the wall of the endotracheal tube. The first lumen 414 is used to deliver medication to the lungs while the second lumen 416 is used to inflate the balloon 410. In order to facilitate the delivery of medication in a spray form, the first lumen 414 is sealed by a membrane which contains a plurality of micro pores 420. This embodiment is particularly effective when the medication needs to be repeatedly administered or when topical anesthetics are necessary.

It is to be understood that the present invention is not limited to the embodiments described above, but encompasses any and all embodiments within the scope of the following claims.

I claim:

1. A mouthpiece for an endotracheal tube comprising:

a bite block of unitary construction having a proximal surface, a distal surface, and a central aperture of a predetermined diameter for receiving an endotracheal tube therethrough;

at least two arresting elements, each of said arresting elements including:

a base portion positionable in a parallel manner along the proximal surface of said bite block; and an upstanding leg integrally attached at one end to said base portion;

means for pivotally coupling each of said arresting elements to said bite block;

frictional engagement means associated with each of said arresting elements for restricting movement of the endotracheal tube; and means for detachably engaging each of said arresting elements to said bite block.

2. A mouthpiece for an endotracheal tube as recited in claim 1 wherein said means for pivotally coupling each of said arresting elements to said bite block comprises a band of flexible material attached at one end to the outermost point on the proximal surface of said bite block and attached at the opposite end to said base portion at a location proximally adjacent its first end.

3. A mouthpiece for an endotracheal tube as recited in claim 1 wherein said means for pivotally coupling comprises a hinge.

4. A mouthpiece for an endotracheal tube as recited in claim 1 wherein each of said arresting elements further includes a shoulder extending from the free end of said upstanding leg.

5. A mouthpiece for an endotracheal tube as recited in claim 1 wherein said means for detachably engaging each of said arresting elements comprises:

a fitted extension originating from said base portion and extending outward and perpendicularly to said base portion; and a mating recess defined in the proximal surface of said bite block for securely receiving said fitted extension.

6. A mouthpiece for an endotracheal tube as recited in claim 1 wherein said frictional engagement means comprises a resilient friction pad attached to the upstanding leg of each of said arresting elements and positioned so as to facilitate being pressed snugly against the endotracheal inserted through said mouthpiece.

7. A mouthpiece for an endotracheal tube as recited in claim 6 wherein each of said friction pads is composed of rubber.

8. A mouthpiece for an endotracheal tube comprising:.

a bite block of unitary construct:ion having a proximal surface, a distal surface, and a central aperture of a predetermined diameter for receiving an endotracheal tube therethrough;

a tubular extension originating from said proximal surface and extending perpendicularly therefrom, said tubular extension having an inner diameter identical to the diameter of the central aperture contained in said bite block and an outer diameter substantially less than the distance from the outermost point on the proximal surface of said bite block to said central aperture;

at least two arresting elements;

means for pivotally coupling each of said arresting elements to said bite block; and frictional engagement means associated with each of said arresting elements for restricting movement of the endotracheal tube.

9. A mouthpiece for an endotracheal tube as recited in claim 8 wherein each of said arresting elements further comprises an arm and a shoulder extending from said arm, and wherein said means for pivotally coupling comprises a hinge disposed at a point where said tubular extension originates.

10. A mouthpiece for an endotracheal tube as recited in claim 8 wherein said frictional engagement means comprises a fitted friction pad originating from each of said arresting elements, and wherein said tubular extension further contains a plurality of mating recesses extending from said inner diameter to said outer diameter for receiving each of said fitted friction pads.

11. An endotracheal system comprising:
   a. an endotracheal tube comprising:
      a proximal end,
      a distal end,
      an exit port integrally attached to said distal end,
      an inner diameter,
      an outer diameter,
      a wall defined by the area formed between said inner and outer diameters,
      an inflatable balloon surrounding said wall at the distal end of said endotracheal tube,
      means for inflating said balloon,
      a first lumen originating external of said endotracheal tube and entering said wall through a first entry point proximate said proximal end of said endotracheal tube, said first lumen extending through said endotracheal tube and terminating at said exit port for delivering medication out of said endotracheal tube,
      a second lumen originating external of said endotracheal tube and entering said wall through a second entry point proximate said proximal end of said endotracheal tube, said second lumen extending through said endotracheal tube and existing in said balloon, and
      a membrane integrally connected to the exit port of said first lumen, said membrane containing a plurality of micro pores dimensioned for atomizing the medication;
   b. a mouthpiece comprising:
      a bite block of unitary construction having a proximal surface, a distal surface, and a central aperture of a predetermined diameter for receiving an endotracheal tube therethrough,
      at least two arresting elements, each of said arresting elements including a base portion positionable in a parallel manner along the proximal surface of said bite block and an upstanding leg integrally attached at one end to said base portion,
      means for pivotally coupling each of said arresting elements to said bite block,
      frictional engagement means associated with each of said arresting elements for restricting movement of said endotracheal tube, and
      means for detachably engaging said arresting elements to said bite block; and
   c. means for securing said endotracheal system to a patient.

12. An endotracheal system as recited in claim 11 wherein each of said arresting elements further comprises a shoulder extending from the free end of said upstanding leg, said shoulder containing a vertical groove.

13. An endotracheal system as recited in claim 12 wherein said means for securing said endotracheal system to a patient comprises umbilical tape wrapped around the vertical groove of the shoulder of a first arresting element, extending behind the neck of a patient, wrapped around the vertical groove of the shoulder of a second arresting element, and said umbilical tape having both of its ends tied together.

14. An endotracheal system as recited in claim 12 further comprising a connector for attaching said endotracheal tube to a gas supply, said connector having a passageway for said gas supply and at least one auxiliary passageway extending into said first passageway.

15. An endotracheal system as recited in claim 14 wherein said means for securing said endotracheal system to a patient comprises umbilical tape wrapped around the vertical groove of the shoulder of a first arresting element, extending behind the neck of a patient, wrapped around the vertical groove of the shoulder of a second arresting element, and wrapped around said connector.

* * * * *